United States Patent [19]
Lichtwardt et al.

[11] Patent Number: 5,902,749
[45] Date of Patent: May 11, 1999

[54] AUTOMATED CHEMICAL METERING SYSTEM AND METHOD

[75] Inventors: Mark Allen Lichtwardt; David Sisneros, both of Lakewood, Colo.

[73] Assignee: The United States of America as represented by the Secretary of the Interior, Washington, D.C.

[21] Appl. No.: 08/933,175

[22] Filed: Sep. 18, 1997

[51] Int. Cl.⁶ .................................................. G01N 35/08
[52] U.S. Cl. ........................... 436/50; 436/43; 436/52; 436/55; 436/56; 436/172; 436/179; 436/180; 422/67; 422/81; 422/82.08; 422/105; 422/110; 422/119
[58] Field of Search .................................. 436/43, 50, 52, 436/55, 56, 174, 179, 180, 800, 172; 422/67, 68.1, 81, 82.08, 105, 110, 119

[56] References Cited

U.S. PATENT DOCUMENTS

| | | | |
|---|---|---|---|
| 3,704,952 | 12/1972 | Bird | 436/56 |
| 3,980,435 | 9/1976 | Wimberley | 422/81 |
| 3,992,109 | 11/1976 | Bock | 356/181 |
| 4,783,314 | 11/1988 | Hoots et al. | 422/3 |
| 5,004,696 | 4/1991 | Clinkenbeard | 436/51 |
| 5,006,311 | 4/1991 | Hoots et al. | 422/62 |
| 5,171,450 | 12/1992 | Hoots | 210/701 |
| 5,266,493 | 11/1993 | Young | 435/55 |
| 5,413,719 | 5/1995 | Sivakumar et al. | 210/708 |
| 5,435,969 | 7/1995 | Hoots et al. | 422/14 |
| 5,565,619 | 10/1996 | Thungstrom et al. | 73/40.7 |
| 5,705,394 | 1/1998 | Ananthasubramanian et al. | 436/55 |

*Primary Examiner*—Long V. Le
*Attorney, Agent, or Firm*—E. Philip Koltos

[57] ABSTRACT

A chemical metering and control system is provided which maintains a desired level of a pesticide (or other chemical) in any open or closed channel flow stream with fluctuating flow rates. The system dispenses an amount of the pesticide at an injection point of the flow stream along with a fluorescent indicating dye, and then takes a sample downstream from the injection point to determine how much of the indicating dye is present in the flow stream, and therefore how much pesticide is present. At the sampling point a pump extracts a flow stream sample and passes the sample to a fluorometer which measures the amount of fluorescent indicating dye injected upstream. A proportional integral derivative (PID) controller then adjusts the level of the pesticide/dye mixture in order to achieve the appropriate concentration of pesticide in the flow stream.

30 Claims, 1 Drawing Sheet

AUTOMATED CHEMICAL METERING SYSTEM AND METHOD

BACKGROUND OF THE INVENTION

1. Field of the Invention

The present invention relates to feedback control systems, and in particular to a control system for maintaining a constant concentration of a chemical being injected into a flow stream having fluctuating flow rates.

2. The Prior Art

One prior art method for automatically controlling the concentration of a chemical in a flow stream uses an ion-selective electrode, a data acquisition system, and specialized computer software. However, the electrodes used in this method often encounter interference from other ionic species, and thus this method is only capable of measurement within a specific limited range of ionic concentrations.

Although the method of the invention is obviously not limited to such an application, an important application is in the treatment of water channels with pesticides in order to destroy, and prevent growth of aquatic site pests such as Sago Pondweed. The current method of controlling the amount of such pesticides injected into a canal over time involves manually adjusting a peristaltic pump. However, many of the canals requiring aquatic site pest control are in areas where flood or spray irrigation is used. Each time water is added or removed from the canal, the flow rate of the canal changes. For this reason, the current method requires continuous monitoring and adjusting of the rate of pesticide injection. Sometimes the pesticide is most effective when injected over a period of 100 hours or more, which necessitates extensive manpower. Not only is this extensive manpower costly, but experience has shown that manual injection of the pesticide is often ineffective and costly as well because it is difficult to maintain proper pesticide concentration in this way.

Another candidate method for controlling the rate of chemical pesticide injection uses a personal computer along with a data acquisition system to monitor canal flow rate or pesticide concentration. A computer program uses this acquired data in order to control the peristaltic pump. However, this method is impractical for the specific applications being considered for at least the following reasons:

1) the majority of the sites where the injection system is to be used are remote and do not have access to the electrical grid power necessary to run the computer or data acquisition system and therefore, a large battery bank or a gas generator is required to meet the high energy demands;
2) it is difficult and expensive to protect a computer and data acquisition equipment from potential vandalism (particularly where left unattended on site for extended periods) and the harmful effects of dust and moisture;
3) highly trained, experienced personnel are required to set up and maintain both the computer and data acquisition system; and
4) the associated capital costs are high.

SUMMARY OF THE INVENTION

In accordance with the invention, a chemical metering and control system is provided which, among other applications, can be used to assist in maintaining a desired level of a chemical pesticide in a flow stream. In this application, the system dispenses an amount of the pesticide mixed with an indicating dye at an injection point along the flow stream and then takes a sample of the flow stream downstream from the injecting point to determine how much indicating dye is present in the flow stream, and, therefore, how much pesticide is present. More specifically, at the sampling point, a pump extracts a flow stream sample and passes the sample to a fluorometer which measures the amount of fluorescent indicating dye injected upstream so that a proportional integral derivative (PID) controller can adjust the level of the pesticide/dye mixture in order to achieve the appropriate concentration of pesticide in the flow stream.

More generally, in accordance with a preferred embodiment of the invention, a system is provided for controlling the amount of a substance to be input into a flow stream, the system comprising: control means for controlling an amount of a combination comprising, in known proportions, an indicator and the substance input into the flow stream at an input point; and an indicator detection means, located downstream in to the flow stream from the input point, for indicating an amount of the indicator, and for determining from the indicator amount, the amount of the substance to be input.

Preferably, the control means maintains a constant concentration of said substance regardless of any changes in properties of said substances, such as changes in viscosity that occur due to temperature changes, by adjusting the amount of said substances input into said flow stream.

In a preferred implementation, the control means further comprises a control pump for pumping the combination into the flow stream, and a PID controller for adjusting the amount of the combination pumped by the control pump.

Preferably, the indicator is a fluorescent dye, such as Rhodamine WT, and the indicator detection means further comprises a fluorometer which measures the fluorescence of the feed water. The indicator detection means has an indicator pump for pumping a sample from the feed water into the fluorometer.

In a further preferred implementation, the system further comprises first and second power means for providing power to the control means and the indicator detection means respectively. The first and second power means can provide alternating current from an electrical power grid or from an inverter connected to a battery. Alternatively, the power means can provide direct current in the form of a battery or a photovoltaic module. In yet another preferred implementation, the system includes a mixing tank for mixing the indicator and the substance whose concentration in the flow stream is to be controlled.

In accordance with a further aspect of the invention, a method is provided for controlling an amount of a chemical introduced into a flow stream, the method comprising: creating a combination by mixing in a known proportion the chemical and an indicator; injecting an amount of the combination into the flow stream at an input point; determining the amount of the indicator in the flow stream at a location downstream from the input point so as to then determine the amount of the chemical in the flow stream; and adjusting, if necessary, the amount of the chemical in the flow stream by altering the amount of the combination injected into the flow stream. In a preferred implementation, the indicator is a fluorescent dye, such as Rhodamine WT, and the determining step further comprises measuring the amount of the dye with a fluorometer and sending a signal to adjust the amount of the combination injected into the flow stream.

In accordance with yet another aspect of the invention, a method is provided for determining the flowrate of a flow stream, the method comprising: providing a substance-indicator combination by mixing a substance and an indicator in known proportions; injecting, at a known rate, an amount of said combination into the flow stream at an input point; determining the concentration of said indicator in the flow stream at a location downstream of said input point; comparing the concentration of indicator in the flow stream with the known proportion of the indicator in the injected combination so as to determine a multiplying factor; and multiplying the injection rate by said multiplying factor to determine the flowrate of the flow stream.

Other features and advantages of the invention will be set forth in, or apparent from, the following detailed description of the preferred embodiments of the invention.

BRIEF DESCRIPTION OF THE DRAWING

The single FIGURE of the drawings is a schematic block diagram of the basic units or components of a system constructed in accordance with a preferred embodiment of the invention.

DETAILED DESCRIPTION OF THE PREFERRED EMBODIMENTS

Figure 1:
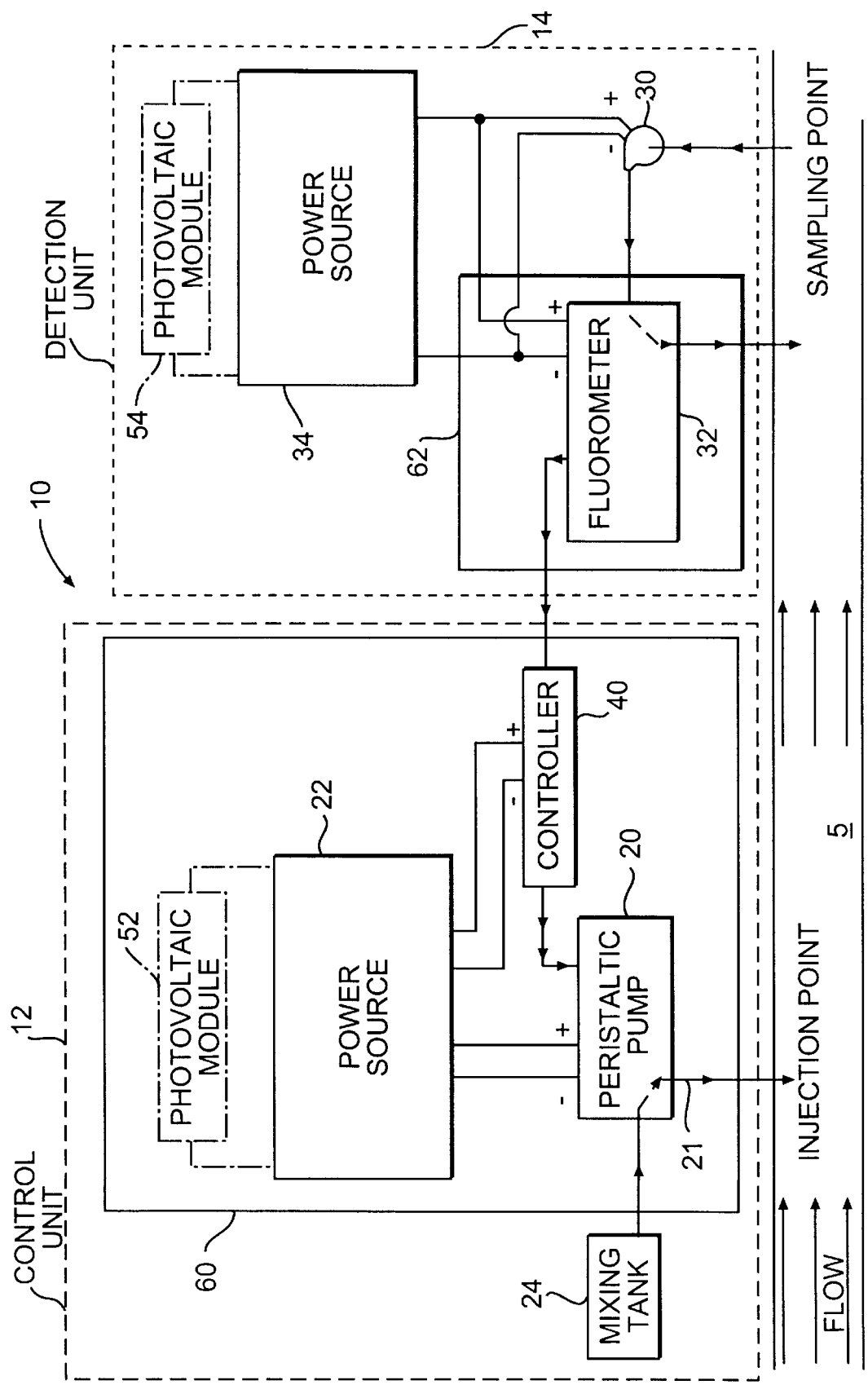

As illustrated, a chemical metering and control system 10 is provided for maintaining in a flow stream 5 a substantially constant concentration of a particular substance or chemical, such as a chemical pesticide. Flow stream 5 has a direction of flow shown by the arrows. As is shown, system 10 basically comprises a control unit 12 and a detection unit 14.

Control unit 12 is used for controlling the amount of a particular substance introduced into flow stream 5. In the discussion below, this substance will be assumed to be a chemical pesticide and the indicator substance to be a fluorescent dye. Control unit 12 comprises a peristaltic pump 20 connected to a power source 22 and a mixing tank 24. Mixing tank 24 contains a combination or mixture of (1) the pesticide that is to be maintained at a particular concentration and (2) the indicator substance, i.e., a fluorescent dye. The proportion of pesticide to dye can be adjusted according to a particular situation, but this proportion is known. Peristaltic pump 20 preferably comprises a digital pump drive/controller that is capable of using an analog input signal such as a 0 to 10 volt direct current or 4 to 20 mA signal, for speed control. A Masterflex 7523-30 digital pump drive with a 7518-60 pump head is suitable. Peristaltic pump 20 pumps the combination from mixing tank 34 through a hose, indicated at 21, into flow stream 5 at an input or injection point.

The combination of pesticide and dye is mixed with the flow stream 5 and travels downstream where detection unit 14 takes a sample of flow stream 5 and detects and measures the amount of dye in flow stream 5. Detection unit 14 is located far enough downstream from control means 12 that complete mixing of the pesticide/dye combination with flow stream 5 takes place before sampling occurs. Detection unit 14 uses a detection pump 30 to pump a fluid sample from flow stream 5 through a flow-through cell (not shown) of a fluorometer 32. Fluorometer 32 detects the amount of fluorescent dye in flow stream 5. A Rule 25D submersible pump can be used as detection pump 30, but other conventional pumps would also be suitable. The fluorometer 32 used in a preferred embodiment of the invention is a Turner Design 10-AU Digital Fluorometer unit having an analog output, and the flow-through cell referred to above. This unit can be used with a data logger, and has a 12 volt DC power source option. Both detection pump 30 and fluorometer 32 are connected to a power source 34. Power source 34 is described in further detail below.

By determining the amount of dye in flow stream 5, the amount of pesticide can be determined based on the previously known proportion of pesticide to dye present in the mixture tank and injected upstream from detection unit 14. Once the amount of dye is determined by measuring the fluorescence of the fluid from flow stream 5, an analog output signal is sent to the control unit 12. Control unit 12 also includes a proportional integral derivative (PID) controller 40 that receives the output signal from fluorometer 32. PID controller 40 preferably comprises a universal input/output controller with an adjustable set point that can be programmed for different proportional bands and response times. The analog input/output of PID controller 40 must be compatible with the other components, such as peristaltic pump 20 and fluorometer 32, so that PID controller 40 can adjust the speed control voltage or current of power pump 20 until the desired concentration of dye (pesticide) is achieved. Since PID controller 40 operates based on desired concentration levels and the system does not rely on flow rates, the present invention operates effectively regardless of changes in properties of the chemical being injected, such as changes in viscosity due to changing temperatures.

Once this desired concentration is accomplished, PID controller 40 will continuously monitor the concentration and make the necessary adjustments to maintain an acceptable concentration level. A suitable controller is a Love Controls Model 16060. PID controller 40 is supplied with power from power source 22.

Power source 22 can be any suitable power source such as the alternating current (AC) power supplied by any nearby electrical grid, or a battery connected to an inverter for converting direct current (DC) from battery to alternating current to be supplied to both peristaltic pump 20 and PID controller 40.

Power source 34 can also be any suitable power supply such as AC power supplied from an electrical power grid or a battery. Power supply 34 supplies power to detection pump 30 and fluorometer 32.

Optionally, a pair of photovoltaic modules 52 and 54 can replace or supplement power supplies 22 and 34. Photovoltaic modules 52 and 54 convert solar energy to charge the batteries of power supplies 22 and 32, respectively, or if there is sufficient solar energy, supply power directly to the system.

An aluminum enclosure 60 encloses peristaltic pump 20, power source 22 and PID controller 40, and a further aluminum enclosure 62 encloses fluorometer 32 in order to protect the equipment within from vandalism, water, dust and lightening.

The system 10 is accurate for any range of flows or concentrations. The accuracy can be optimized by using the proper size of hose 21 with the peristaltic pump 20, by adjusting the programming parameters in PID controller 40 and fluorometer 32, and by changing the ratio of chemical to dye in the mixing tank 24.

As mentioned above, in accordance with a further aspect of the invention, the system 10 can be used as a flowmeter. In this regard, the amount of substance (e.g. chemical) and indicator being injected is directly proportional to the flow rate of the canal or flowstream into which the substance-indicator combination is injected. Thus, the system 10 can be used as a flowmeter for both open and closed channel flowstreams by taking the injection rate from the injection pump 20 (the injection rates is set and, therefore, known) and multiplying this rate by a multiplying or scaling factor. This factor can be readily determined by measuring the concentration of the indicator in the flowstream and comparing this with the known percent of indicator present in the substance-indicator solution in the mixing tank 24. This method works best when using a nonviscous indicator and under such conditions is more accurate than prior art methods.

In addition to the applications discussed above, the system of the invention can also be used in absorption studies to determine the rates at which different chemicals, dyes, or indicators are absorbed by different plant species. Further, the system can be used to determine seepage (qualitative and quantitative) of chemicals/water from one water source to an adjacent water source such as the seepage between an irrigation canal and a river. This can be accomplished by injecting a known concentration of indicator into one of the water sources using the chemical metering and control system of the invention and then mindicator in the indicator in the other water source. Other applications include mosquito abatement in static and flowing water systems, maintaining essential nutrients in large aquatic systems (i.e. aquariums), determination of water current patterns in lakes and river systems, reduction of nutrients in output water from animal processing plants/irrigations systems, and reduction of toxic metals in output water from new and old mining operations which flow into rivers and lakes. There are additional applications in the food processing and medical industries.

Although the present invention has been described in relation to specific exemplary embodiments thereof, it will be understood by those skilled in the art that variations and modifications can be effected in these exemplary embodiments without departing from the scope and spirit of the invention.

What is claimed is:

1. A system for controlling the amount of a substance input into a flow stream, said system comprising:
    control means for controlling an amount of a combination comprising, in known proportions, an inert indicator and said substance input into said flow stream at an input point; and
    an indicator detection means, located in said flow stream downstream from said input point downstream, for obtaining a sample from said flow stream, for indicating the amount of said inert indicator in said sample, and for determining from said indicator amount, the amount of said substance input into the flow stream.

2. A system according to claim 1 wherein said control means further comprises a control pump for pumping said combination, and a controller, responsive to said indicator detection means, for adjusting the amount of said combination pumped by said control pump.

3. A system according to claim 2 wherein said indicator is an inert fluorescent dye and said indicator detection means comprises a fluorometer which measures the fluorescence of said sample.

4. A system according to claim 3 wherein said indicator detection means further comprises an indicator pump for pumping said sample into said fluorometer.

5. A system according to claim 4 further comprising first and second power supply means for providing power to said control means and said indicator detection means, respectively.

6. A system according to claim 5 further comprising a first enclosure enclosing said first power supply means, said controller, and said control pump, and a second enclosure enclosing said fluorometer.

7. A system according to claim 5 wherein said first and second power supply means provide alternating current to said control means and said indicator detection means, respectively.

8. A system according to claim 5 wherein said second power supply means comprises a detection battery for providing direct current to said indicator detection means.

9. A system according to claim 5 wherein said first and second power supply means comprise a photovoltaic module for providing direct current to said system.

10. A system according to claim 5 wherein said first power supply means comprises a control battery connected to an invertor for transforming said direct current from said battery to alternating current.

11. A system according to claim 10 further comprising a photovoltaic module for providing direct current to at least one of said control battery and said detection battery to provide charging thereof.

12. A system according to claim 1 further comprising a mixing tank for mixing said indicator and said substance.

13. A system according to claim 1 wherein said indicator is Rhodamine WT dye.

14. A system according to claim 2 wherein said control means maintains a constant concentration of said substance regardless of any changes in properties of said substance, such as changes in viscosity that occur due to temperature changes, by adjusting the amount of said substances input into said flow stream.

15. A system for controlling the amount of a chemical pesticide injected into a flow stream, said system comprising:
    a mixing tank containing a mixture, in known proportions, of the chemical pesticide to be injected and an inert fluorescent dye;
    a peristaltic pump for injecting said mixture into said flow stream at a first location therealong;
    a controller for controlling the operation of said pump;
    detection means located at a second location downstream from said first location and including a fluorometer, for obtaining a sample of said flow stream at said second location and for producing an output signal related to the amount of said inert fluorescent dye in said sample; and
    means for connecting said detection means to said controller so that the controller controls the operation of said pump in accordance with said output signal.

16. A method of controlling the amount of a chemical introduced into a flow stream, said method comprising:
    creating a combination by mixing, in a known proportion, said chemical and an inert indicator;
    injecting an amount of said combination into said flow stream at an input point;
    determining the amount of said inert indicator in said flow stream at a location downstream from said input point;
    determining from the amount of said indicator in said flow stream the amount of said chemical in said flow stream; and
    adjusting, as necessary, the amount of said chemical in said flow stream by altering the amount of said combination injected into said flow stream based on the determined amount of said chemical.

17. A method according to claim 16 wherein said indicator is an inert fluorescent dye, and said determining step further comprises measuring the amount of said dye with a fluorometer, and using a signal based on measuring the amount of said dye to adjust said amount of said combination injected into said flow stream.

18. A method of determining the flowrate of a flow stream, said method comprising:

produce a substance-indicator combination by mixing a substance and an inert indicator in known proportions;

injecting, at a known injection rate, an amount of said combination into said flow stream at an input point;

determining the concentration of said indicator in said flow stream at a location downstream of said input point;

comparing the concentration of said inert indicator in said flow stream with the known proportion of said inert indicator in the combination being injected so as to determine a multiplying factor; and multiplying the known injection rate by said multiplying factor to determine the flowrate of the flow stream.

19. A system for controlling the amount of a substance input into a flow stream, said system comprising:

control means for controlling an amount of a combination comprising, in known proportions, an indicator and said substance, input into said flow stream at an input point; and an indicator detection means, located in said flow stream downstream from said input point, for obtaining a sample from said flow stream, for indicating the amount of said indicator in said sample, and for determining from said indicator amount, the amount of said substance input into the flow stream, said control means comprising a control pump for pumping said combination into the flow stream and a proportional integral derivative controller, responsive to said indicator means, for adjusting the amount of said combination pumped by said control pump, and said indicator detection means comprising a fluorometer for measuring the fluorescence of said sample, and an indicator pump for pumping said sample from the flow stream into said fluorometer.

20. A system according to claim 19 further comprising first and second power supply means for providing power to said control means and said indicator detection means, respectively.

21. A system according to claim 20 further comprising a first enclosure enclosing said first power supply means, said controller, and said control pump, and a second enclosure enclosing said fluorometer.

22. A system according to claim 20 wherein said first and second power supply means provide alternating current to said control means and said indicator detection means, respectively.

23. A system according to claim 20 wherein said second power supply means comprises a detection battery for providing direct current to said indicator detection means.

24. A system according to claim 20 wherein said first and second power supply means comprise a photovoltaic module for providing direct current to said system.

25. A system according to claim 20 wherein said first power supply means comprises a control battery connected to an invertor for transforming said direct current from said battery to alternating current.

26. A system according to claim 25 further comprising a photovoltaic module for providing direct current to at least one of said control battery and said detection battery to provide charging thereof.

27. A system according to claim 19 further comprising a mixing tank for mixing said indicator and said substance.

28. A system according to claim 19 wherein said indicator is Rhodamine WT dye.

29. A system according to claim 19 wherein said control means maintains a constant concentration of said substance regardless of any changes in properties of said substance, such as changes in viscosity that occur due to temperature changes, by adjusting the amount of said substances input into said flow stream.

30. A system for controlling the amount of a chemical pesticide injected into flowing water in a water channel in an outdoor environment, said system comprising:

a mixing tank containing a mixture, in known proportions, of the chemical pesticide to be injected and a fluorescent dye;

a first, peristaltic pump for injecting said mixture into the water of the water channel at a first location therealong;

a controller for controlling the operation of said pump;

a second, sampling pump, located at a second location along the water channel downstream from said first location, for obtaining a sample of the water in the water channel at said second location, a fluorometer connected to said sampling pump for receiving said sample from said sampling pump and for producing an output signal related to the amount of dye in said sample; and means for connecting said fluorometer to said controller so that the controller controls the operation of said first pump in accordance with said output signal.

* * * * *